United States Patent [19]

Pöchlauer et al.

[11] Patent Number: 6,031,123
[45] Date of Patent: Feb. 29, 2000

[54] PROCESS FOR STABILIZING CYANOHYDRINS

[75] Inventors: Peter Pöchlauer, Linz; Irma Wirth, Enns; Rudolf Neuhofer, Mittertreffling, all of Austria

[73] Assignee: DSM Fine Chemicals Austria GmbH, Austria

[21] Appl. No.: 09/310,856

[22] Filed: May 13, 1999

[30] Foreign Application Priority Data

May 14, 1998 [AT] Austria ............................. 827/98

[51] Int. Cl.$^7$ ............................. C07L 255/00
[52] U.S. Cl. ............................. 558/304
[58] Field of Search ............................. 558/304

[56] References Cited

U.S. PATENT DOCUMENTS 4,590,013  5/1986  Maloney et al. .

FOREIGN PATENT DOCUMENTS 585644  2/1947  United Kingdom .

*Primary Examiner*—Johann Richter
*Assistant Examiner*—Joseph Murray
*Attorney, Agent, or Firm*—Wenderoth, Lind & Ponack, L.L.P.

[57] ABSTRACT

A process for stabilizing enantiomer-enriched cyanohydrins where citric acid and/or boric acid or boric anhydride is added as a stabilizer to the cyanohydrin to be stabilized.

5 Claims, No Drawings

PROCESS FOR STABILIZING CYANOHYDRINS

Cyanohydrins are of importance, for example, for synthesizing alpha-hydroxy acids, alpha-hydroxy ketones, beta-amino alcohols, which are used for obtaining biologically effective substances, for example pharmaceutically active substances, vitamins or else pyrethroid compounds.

Since cyanohydrins are instable per se and tend to decompose in a reversal of their formation reaction, various additives have been used to stabilize them. Thus, in industry, preference is given to using sulfuric acid and phosphoric acid (Ullmans Enzyklopädie der techn. Chemie, 4th Edition, Vol. 7, p. 33). U.S. Pat. No. 4,299,843 discloses the use of other acids, such as, for example, HCl, toluenesulfonic acid, acetic acid, propionic acid, etc. However, the acids which have hitherto been described can not ensure sufficient stabilization of the content and the enantiomeric excess in the case of prolonged storage, or when the cyanohydrins undergo thermal stress. It was therefore the object of the invention to find better stabilizers.

The invention provides a process for stabilizing enantiomer-enriched cyanohydrins, which comprises adding citric acid and/or boric acid or boric anhydride to the cyanohydrin to be stabilized.

According to the invention, citric acid and/or boric acid or boric anhydride are added to the pure enantiomer-enriched cyanohydrin or to a solution of this cyanohydrin in an amount which is sufficient for stabilization, to suppress a reconversion into HCN and the parent carbonyl compound or a loss of enantiomeric excess as long as possible. This is of great importance, in particular during distillation, storage or formulation. The amount of acid that is added can depend on the cyanohydrin to be stabilized. However, an addition of from 0.01 to 5% by weight of acid, based on the cyanohydrin, is sufficient. The corresponding cyanohydrin is preferably stabilized with from 0.02 to 1% by weight of acid. Here, citric acid and boric acid or boric anhydride can be employed each on his own, but also in combination, in the abovementioned concentration range. Boric anhydride is preferably employed in cases where the cyanohydrin is possibly contaminated with water from its synthesis reaction. This water then forms boric acid with boric anhydride.

The stabilizers according to the invention are suitable for stabilizing enantiomer-enriched cyanohydrins obtained, for example, by reaction of an aldehyde or a ketone, a cyanide group donor and a hydroxynitrile lyase.

Aldehydes are to be understood as aliphatic, aromatic or heteroaromatic aldehydes. Aliphatic aldehydes are to be understood as saturated or unsaturated aliphatic, straight-chain, branched or cyclic aldehydes. Preferred aliphatic aldehydes are straight-chain aldehydes having in particular 2 to 18 C atoms, preferably from 2 to 12, which are saturated or mono- or polyunsaturated. The aldehyde can have both C—C double-bonds and C—C triple bonds. The aldehyde can be unsubstituted or substituted by groups which are inert under the reaction conditions, for example by unsubstituted or substituted aryl or heteroaryl groups, such as phenyl or indolyl groups, by halogen, ether, alcohol, acyl, carboxylic acid, carboxylic ester, nitro or azido groups.

Examples of aromatic or heteroaromatic aldehydes are benzaldehyde or variously substituted benzaldehydes, such as, for example, 3,4-difluorobenzaldehyde, 3-phenoxybenzaldehyde, 4-fluoro-3-phenoxybenzaldehyde, furthermore furfural, anthracene-9-carbaldehyde, furan-3-carbaldehyde, indol-3-carbaldehyde, naphthalene-1-carbaldehyde, phthalaldehyde, pyrazole-3-carbaldehyde, pyrrole-2-carbaldehyde, thiophene-2-carbaldehyde, isophthalaldehyde, etc.

Ketones are aliphatic, aromatic or heteroaromatic ketones where the carbonyl carbon atom is substituted asymmetrically. Aliphatic ketones are to be understood as saturated or unsaturated, straight-chain, branched or cyclic ketones. The ketones can be saturated or mono- or polyunsaturated. They can be unsubstituted or substituted by groups which are inert under the reaction conditions, for example by unsubstituted or substituted aryl or heteroaryl groups, such as phenyl or indolyl groups, by halogen, ether, alcohol, acyl, carboxylic acid, carboxylic ester, nitro or azido groups.

Examples of aromatic or heteroaromatic ketones are acetophenone, indolylacetone, etc.

Enantiomer-enriched cyanohydrins are to be understood as those cyanohydrins which contain the (S)- or (R)-form in a percentage of more than 50%, preferably more than 90%.

The stabilizers according to the invention are preferably suitable for stabilizing aliphatic and aromatic enantiomer-enriched cyanohydrins, such as, for example, (R)- or (S)-3-phenoxybenzaldehyde cyanohydrin, (R)- or (S)-4-fluoro-3-phenoxybenzaldehyde cyanohydrin, (R)- or (S)-3,4-difluorobenzaldehyde cyanohydrin, (R)- or (S)-2-hydroxy-2,3-dimethylbutanonitrile, (R)- or (S)-2-hydroxy-2-methylpentanonitrile, (R)- or (S)-2-hydroxynonanonitrile, (R)- or (S)-2-hydroxy-2-methylphenylacetonitrile, (R)- or (S)-mandelonitrile.

The cyanohydrins to be stabilized may also be present as a solution. Here, solvents are those which are also employed during the preparation process. These are, for example, aliphatic or aromatic hydrocarbons, which may optionally be halogenated, alcohols, ethers or esters or mixtures thereof. Preference is given to methyl tert-butyl ether (MTBE), diisopropyl ether, dibutyl ether, ethyl acetate or mixtures thereof.

The stabilizers according to the invention distinguish themselves in particular at elevated temperatures of from 70 to 110° C. By addition of citric acid and/or boric acid or boric anhydride, the content and the enantiomeric excess of the (R)- or (S)-cyanohydrins decreases, even at high temperatures and over a relatively long period of time, considerably less than when customary additives known from the prior art are used.

EXAMPLE 1

10 g of (S)-3-phenoxybenzaldehyde cyanohydrin (SCMB) were admixed with 50 mg of acid, and the content and the enantiomeric excess at 80° C. and 100° C. were determined over a period of time of 23 h.

The mixture was continuously stirred during the period of observation.

The following acids were used:

citric acid ($H_2O$ -free)
boric anhydride
and for comparison
$H_2SO_4$
$H_3PO_4$
The results are shown in Tables 1 and 2

TABLE 1

| | % ee (enantiomeric excess) | | | | | |
|---|---|---|---|---|---|---|
| Stabilizer | Citric acid | | Boric anhydride | | H₂SO₄ | H₃PO₄ |
| Hours | 80° C. | 100° C. | 80° C. | 100° C. | 100° C. | 100° C. |
| 0 | 98.6 | 98.6 | 98.6 | 98.6 | 92.6 | 92.6 |
| 1 | 98.6 | 98.6 | 98.6 | 98.6 | 87.8 | 91.8 |
| 2 | 98.6 | 98.7 | 98.6 | 98.6 | 86.8 | 92.2 |
| 3 | 98.6 | 98.7 | 98.6 | 98.6 | 86.6 | 91.5 |
| 5 | 98.6 | 98.6 | 98.7 | 98.7 | 86.7 | 90.5 |
| 6 | 98.6 | 98.6 | 98.6 | 98.7 | — | — |
| 7 | 98.5 | 98.6 | 98.6 | 98.6 | 86.6 | 89.2 |
| 8 | 98.7 | 98.6 | 98.7 | 98.6 | 87.9 | 88.4 |
| 23 | 98.7 | 98.1 | 98.7 | 98.6 | 42.1 | 70.8 |

TABLE 2

| | % content | | | | | |
|---|---|---|---|---|---|---|
| Stabilizer | Citric acid | | Boric anhydride | | H₂SO₄ | H₃PO₄ |
| Hours | 80° C. | 100° C. | 80° C. | 100° C. | 100° C. | 100° C. |
| 0 | 98 | 98 | 98 | 98 | 96.8 | 96.8 |
| 1 | 97.9 | 97.6 | 97.6 | 97.7 | 93.5 | 96.1 |
| 2 | 97.7 | 97.2 | 97.6 | 97.6 | 92.6 | 96.4 |
| 3 | 97.7 | 96.8 | 97.8 | 97.6 | 92.3 | 95.7 |
| 5 | 97.5 | 96.3 | 97.6 | 96.3 | 92.4 | 94.7 |
| 6 | 97.4 | 96 | 96.9 | 97 | — | — |
| 7 | 97.4 | 95.6 | 98 | 97 | 92.4 | 93.3 |
| 8 | 92.3 | 95.5 | 87.8 | 96.9 | 93.6 | 92.7 |
| 23 | 96.8 | 91.9 | 97.3 | 95.6 | 74.9 | 81.6 |

EXAMPLE 2

By the method of Ex. 1, 2 g of (S)-4-fluoro-(3)-phenoxybenzaldehyde cyanohydrin were admixed with 10 mg of acid, the mixture was stirred and the content and the enantiomeric excess at 100° C. were determined.

The acids used were once more citric acid and boric anhydride, and H₃PO₄ for comparison.

The results are shown in Table 3.

TABLE 3

| | Citric acid | | Boric anhydride | | H₃PO₄ | |
|---|---|---|---|---|---|---|
| Stabilizer Hours | % ee | % content | % ee | % content | % ee | % content |
| 0 | 91.1 | 97.2 | 91.1 | 97.2 | 91.1 | 97.2 |
| 1 | 91.1 | 96 | 91 | 96.3 | 91 | 96.5 |
| 2 | 91.1 | 95.1 | 91 | 95.1 | 91 | 95.8 |
| 4 | 91.1 | 93.9 | 91 | 93.3 | 91.1 | 95.1 |
| 6 | 91 | 92.4 | 91 | 91.6 | 91.1 | 93.2 |
| 7 | 91 | 91.8 | 90.9 | 91 | 91 | 91.9 |
| 8 | 90.9 | 91.2 | 90.7 | 90.2 | 91 | 90.9 |
| 24 | 87.4 | 78.5 | 88.9 | 83.8 | 84 | 76.3 |

EXAMPLE 3

By the method of Ex. 1, 2 g of (S)-2-hydroxynonanonitrile were admixed with 10 mg of citric acid, the mixture was stirred and the content and the enantiomeric excess at 100° C. were determined. The results are shown in Table 4.

TABLE 4

| | without stabilizer | | with citric acid | |
|---|---|---|---|---|
| Hours | % ee | % content | % ee | % content |
| 0 | 93.3 | 93.8 | 93.3 | 93.8 |
| 1 | 93.2 | 95.2 | 93.2 | 96.8 |
| 3 | 92.8 | 93 | 93.3 | 94.4 |
| 4 | 91.9 | 92.4 | 93.4 | 94.7 |
| 20 | 82.5 | 91 | 93.2 | 96.5 |
| 24 | 75.2 | 90.3 | 93.2 | 95.1 |
| 44 | 45.5 | 72.8 | 91 | 94.9 |

On addition of 10 mg of H₂SO₄ or methanesulfonic acid, the color of the nitrile changed to brown, when the stabilizer used was citric acid, no discoloration occurred.

We claim:

1. A process for stabilizing enantiomer-enriched cyanohydrins, which comprises adding citric acid and/or boric acid or boric anhydride as a stabilizer to the cyanohydrin to be stabilized.

2. The process as claimed in claim 1, wherein from 0.01 to 5% by weight of stabilizer are added.

3. The process as claimed in claim 1, wherein the stabilizer is added to the pure cyanohydrin or to a solution of the cyanohydrin to be stabilized.

4. The process as claimed in claim 1, wherein the stabilizer is added to an aromatic or aliphatic (R)- or (S)-cyanohydrin.

5. The process as claimed in claim 1, wherein the stabilizer is added to an (R)- or (S)-3-phenoxybenzaldehyde cyanohydrin, (R)- or (S)-4-fluoro-3-phenoxybenzaldehyde cyanohydrin, (R)- or (S)-3,4-difluorobenzaldehyde cyanohydrin, (R)- or (S)-2-hydroxy-2,3-dimethylbutanonitrile, (R)- or (S)-2-hydroxy-2-methylpentanonitrile, (R)- or (S)-2-hydroxynonanonitrile, (R)- or (S)-2-hydroxy-2-methylphenylacetonitrile, (R)- or (S)-mandelonitrile.

* * * * *